ized software identification, the software is utilized for diagnostic or service purposes. Other use of the software is blocked and the identification of any software sought to be entered is stored in the memory (32). To initiate a CT scan, a ready button (40) starts a timer (44) which enables a start button (42) to control the power to the CT scanner for a selected short duration, e.g. 30 seconds.

United States Patent [19]

Cecil et al.

[11] Patent Number: 4,991,193
[45] Date of Patent: Feb. 5, 1991

[54] SYSTEM SAFETY MONITOR FOR CT SCANNERS

[75] Inventors: Robert A. Cecil, Solon; Nicholas C. Wislocki, Cleveland; Micheal J. Petrillo, Euclid, all of Ohio

[73] Assignee: Picker International, Inc., Highland Hts., Ohio

[21] Appl. No.: 276,145

[22] Filed: Nov. 25, 1988

[51] Int. Cl.⁵ .............................................. H05G 1/54
[52] U.S. Cl. ..................................... 378/117; 378/96; 378/118; 378/4
[58] Field of Search ................ 378/117, 118, 114–116, 378/96–98, 4; 364/200, 285.4, 286.5, 286.6, 900, 918.7

[56] References Cited

U.S. PATENT DOCUMENTS

| | | | |
|---|---|---|---|
| 4,032,789 | 6/1977 | Workman | 378/117 |
| 4,135,247 | 1/1979 | Gordon et al. | 364/414 |
| 4,158,138 | 6/1979 | Hellstrom | 250/402 |
| 4,260,894 | 4/1981 | Neumann | 250/445 |
| 4,386,320 | 5/1983 | Lafrance | 378/117 |
| 4,442,486 | 4/1984 | Mayer | 364/200 |
| 4,775,993 | 10/1988 | Kaul et al. | 378/91 |

FOREIGN PATENT DOCUMENTS 0084441 1/1983 European Pat. Off. .
WO85/04032 9/1985 PCT Int'l Appl. .

Primary Examiner—Carolyn E. Fields
Assistant Examiner—David P. Porta
Attorney, Agent, or Firm—Fay, Sharpe, Beall, Fagan, Minnich & McKee

[57] ABSTRACT

A gantry (A) of a CT scanner system has an x-ray tube (10) and radiation detectors (14) which produce patient diagnostic data. An operator using a keyboard (20) or other manual controls operates the x-ray tube and other components of the gantry. The operator also causes a central processing unit (C) to process the diagnostic data with a selected algorithm to provide diagnostic information for display on a display (24). The same keyboard and displays are also utilized in routine service and repair processes. A system monitor (E) compares operating conditions sensed by sensors (50), such as operating temperatures and compares them with acceptable operating conditions. When the sensed conditions are unacceptable, a timer (60) is started and shuts down (68) gantry operation after a preselected duration. The operator can override (72) the timed shut down, but each such override is recorded (74) in permanent storage (32). The comparing means also compares software identification codes either for software selected on touch sensitive areas (76) of the display screen or from new software identifications read on a disk drive (22). If the identification of the requested or received software matches an author 18 Claims, 2 Drawing Sheets

SYSTEM SAFETY MONITOR FOR CT SCANNERS

BACKGROUND OF THE INVENTION

The present invention relates to the art of equipment safety and protection monitoring. The invention finds particular application in conjunction with CT scanners and will be described with particular reference thereto. However, it is to be appreciated that the invention is also applicable to other medical diagnostic scanners, such as magnetic resonance scanners, digital x-ray scanners, and the like. Further, the present invention may also find utility in conjunction with other computer based or controlled equipment.

Heretofore, CT scanners have commonly included a gantry system in which the x-ray tube, radiation detectors, x-ray tube assembly rotation motors, cooling equipment, and other associated hardware and controls were mounted. A central processing unit was commonly mounted in another cabinet but interconnected electronically with the gantry. The central processing unit included the computer software and memory for processing radiation intensity data from the gantry to generate image representations and other diagnostic information. The central processing unit could also contain service and set-up software or memory capacity for loading such service software. An operator control panel included the appropriate control buttons, switches, disk drives, display monitors, and the like such that the operator could cause the gantry to take one or more CT scans. The operator control panel also accessed the appropriate software in the central processing unit to process the CT data and generate selected images or other diagnostic displays. For system tune-up and repair, service software could be entered through the disk drives on the console. Appropriate commands from the keyboard controlled the service software and entered software based corrections. System malfunctions or failures could be indicated on the console display or by LED lights located in the console and the central processing unit.

Although the prior art CT scanners indicated abnormal and potentially injurious operating conditions, the operator was under no compulsion to heed the warnings. Rather, the operator could continue to operate the system even under such abnormal operating conditions as overheating of the x-ray tube, overheating of the radiation detectors, and other conditions that could damage or destroy expensive hardware components. For patient safety, it was generally considered inappropriate to overrule the operation and shut-down the CT scanner system when components were operating a temperature or other range that would cause premature but not imminent failure. The patient in the scanner, in some instances, was in a life threatening situation in which the CT scans were a necessary diagnostic tool. This concern for patient safety which allowed operations of the scanners outside of normal operating parameters tended to increase requests for warranty repairs.

Another problem with the prior art CT scanners resided in the use of unauthorized software. For example, third party service technicians could enter and use their own software which improperly or inadequately diagnosed system errors. Even if the manufacturer's software was permanently stored in the CPU and could be accessed, third party technicians often misused the software, improperly diagnosed system failures or miscalibrated the system. As another example, third party image data processing software not designed for this hardware and pirate copies of software designed for this hardware could be entered into the CPU. The use of third party image or patient data software designed for other hardware could cause inaccurate and even incorrect diagnostic readings. Moreover, use of third party and pirate software caused a major financial loss to the manufacturers. The very high number of man hours that go into software development and improvement represent a high cost to the manufacturers which is amortized over copies of the software as it is sold. Pirate software not only cost sales to the manufacturers, but also reduces the number of software copies over which the development costs are amortized—hence, raises costs to honest purchasers.

Commonly, CT scanners have a single push-button for starting a scan. Once the button is pushed, the scan routine is automatically started and completed irradiating the scan circle with radiation. If the scan is inadvertently started, any portion of a patient or technician in the scan circle is needlessly irradiated.

The present invention contemplates a new and improved safety monitor system for CT scanners which overcomes the above referenced problems and others.

SUMMARY OF THE INVENTION

In accordance with the present invention, a medical diagnostic scanner system is provided. The system includes a gantry which receive the patient and performs a non-invasive examination thereof. A central processing unit processes data from the gantry to producing image representations and to assist in various equipment set-up, calibration, failure repair, and other techniques. An operator console includes the appropriate controls for controlling the CPU and gantry to perform various medical imaging techniques, as well as service, set-up, and repairs. A system monitor means interconnects the gantry, CPU, and console to monitor and regulate the operation of the scanner.

In accordance with a more limited aspect of the present invention, a plurality of monitors are provided for monitoring preselected operating conditions. For example, sensors may be provided to sense console operating conditions and the like. A comparing means compares each sensed condition with preselected standards. Upon sensoring a condition which is potentially, but not imminently, injurious to the scanner, the comparing means warns the operator of the malfunction and starts a timer. After a preselected duration, the timer causes a power down sequence to be initiated. The operator has an override control for deactivating or resetting the timer if the operator deems it necessary to continue a scan sequence in spite of the potential injury to the machine. A recording means maintains a record of each override.

In accordance with another more limited aspect of the present invention, the system monitor includes a software identification comparing means for comparing the identifications of software routines requested by the operator or serviceman with an authorized software table. The software request may be made by keyboard entry or by inserting a software disk or tape in a disk drive or tape reader. If the software identification comparing means determines that the software is authorized, it enables the central processing unit to perform the requested software routines. If the software is unauthorized, it is blocked from entering the central processor unit and a recording means records the identification of the unauthorized software.

In accordance with another aspect of the present invention, a two step procedure is required to start a radiation scan. Two buttons or switches are provided which must be depressed within a preselected duration in order to initiate a scan. For example, depressing a ready button enables a start scan button to turn on a gantry power control means. If the start scan button is not depressed within a preselected duration, e.g. 30 seconds, a timer disables the scan button from turning on the power control means. In this manner, unintentionally radiating a subject or technician by inadvertently bumping the start scan switch is eliminated.

One advantage of the present invention is that it automatically shuts down the scanner before damage occurs.

Another advantage of the present invention is that it permits an operator to override an automatic scanner shut down for medical necessity.

Another advantage of the present invention is that it blocks the entry and use of unauthorized software.

Another advantage of the present invention is that it assures patient safety and diagnostic accuracy.

Another advantage of the present invention is that it prevents unauthorized tampering with system software.

Another advantage of the present invention is that it prevents inadvertent irradiation of patients and technicians.

Still further advantages of the present invention will become apparent to those of ordinary skill in the art upon reading and understanding the following detailed description.

BRIEF DESCRIPTION OF THE DRAWINGS

The invention may take form in various components and arrangements of components or in various steps and arrangements of steps. The drawings are only for purposes of illustrating operation of a preferred embodiment and are not to be construed as limiting the invention.

DETAILED DESCRIPTION OF THE PREFERRED EMBODIMENT

Figure 1:
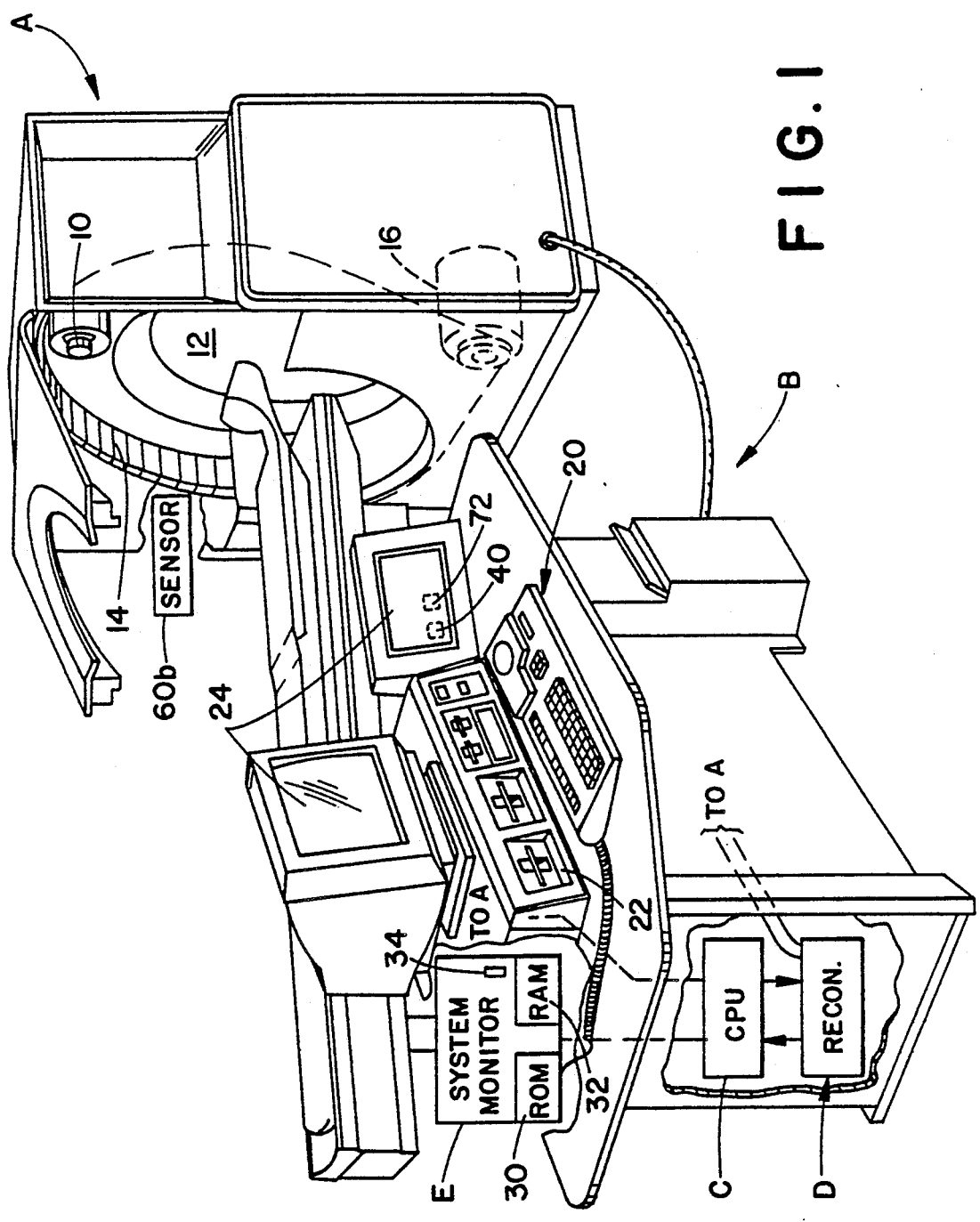
FIG. 1 is a diagrammatic illustration of a CT scanner assembly in accordance with the present invention.

With reference to FIG. 1, a medical diagnostic scanner includes a gantry or examination station A which is interconnected with and operated by console controls B and software of a central processing unit C. The central processing controls the flow of data in a reconstruction and imaging multiprocessor system D. The reconstruction and multiprocessor system has dedicated units for image reconstruction, image display, and gantry control. A system monitor E interconnects with the central processing unit, the gantry and the control panel to monitor their operation. The patient examination apparatus or gantry A, in the preferred embodiment is a computerized tomographic scanner. It includes an x-ray or other radiation source 10 for projecting a fan beam of radiation across a scan circle or examination region 12. An array of detectors 14 are mounted across the examination region from the x-ray source to receive incident radiation that has traversed the scan circle and produce output signals indicative of the radiation intensity. A rotating means 16 rotates the fan beam of radiation around the examination region.

The operator panel B includes a keyboard 20 with which the operator can control operation of the gantry, access diagnostic or service software in the central processing unit, and the like. Software access to the central processing unit is also provided by a disk drive 22 which receives disks for storing patient examination data as well as disks for entering new software or modifying existing software. Operator displays 24 provide man-readable displays of diagnostic images and other patient diagnostic and system malfunction information during patient scan procedures. In the preferred embodiment, one display includes a touch sensitive screen that not only displays information but receives operator input and control commands. The touch sensitive screen is controlled by the CPU which interfaces it with the rest of the system. However, for simplicity of illustration, the touch sensitive input controls are illustrated as being directly connected with the means that each controls. During service procedures, the same displays provide displays of service related information and receive service control commands. The man-readable displays 24 provide man-readable indications of abnormal and potentially deleterious operating conditions.

The reconstruction and imaging multiprocessor system D includes conventional software, firmware, and hardware, for reconstructing image representations from the gantry data. For CT scanners, the software commonly includes an array processor which operates on each view of data with a filter or convolution function and a backprojector for backprojecting the convolved CT scanner data into an image memory. Various image enhancement routines, as are known in the art, may also be incorporated. The central processing unit C not only controls the multiprocessor system D but also has appropriate memory, and where appropriate firmware and hardware, for a serviceman to enter and run conventional service routines. Alternately, the central processing unit may be preprogrammed with these routines.

Figure 2:
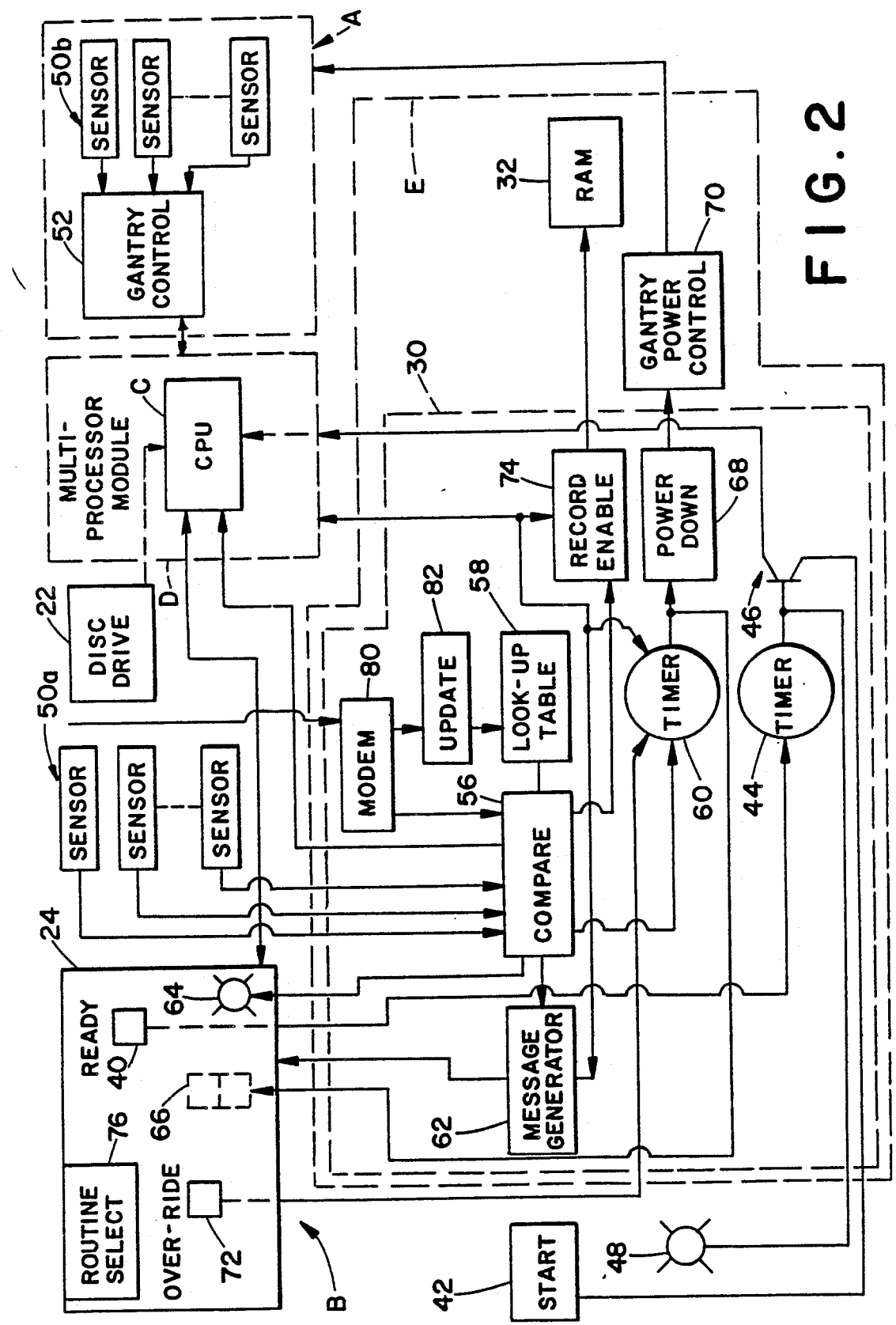
FIG. 2 is a functional block diagram of the system monitor and related portions of the gantry, console, and central processing unit of FIG. 1.

With continuing reference to FIG. 1 and particular reference to FIG. 2, the system monitor means E includes a plurality of routines which are stored in a nonvolatile read only memory 30. The read only memory (ROM) is configured such that it is unreadable if removed from the mounting card. A random access memory 32 provides storage for reporting various monitored system conditions. A battery back-up 34 provides operating power to maintain the information stored in the RAM memory 32 even when the system is shut-off or disconnected.

The scanner includes a two button or two step scan initiation system. A first control area or ready button 40 is defined on the touch sensitive screen and a second control or start scan button 42 is connected to the system monitor. Touching the ready area of the screen enables operation of the start control 42 to initiate a patient scan. More specifically, touching the ready button display causes a timer 44 to close a switch or enabling means 46 to connect the start scan control 42 to the multiprocessing module D to control the gantry A for a preselected duration, e.g. 30 seconds. The timer changes the display, e.g. lights an indicator lamp 48 associated with the start scan button 42 whenever it is enabled. In this manner, depressing the ready control 40 causes the start control 42 and the light 48 to be enabled for 30 seconds. If the operator presses the start button 42 within 30 seconds, a scan will commence. If the start button 42 is not pressed within 30 seconds, the timer 44 will time out and the ready button 40 must again be depressed before a scan can be commenced. In this manner, actuation of the x-ray tube by an operator or technician who accidentally bumps the start button is inhibited.

The system monitor E is interconnected with a plurality of sensors 50a for sensing various console operating conditions and indirectly connected through software to a plurality of sensors 50b for monitoring gantry operating conditions. In the preferred embodiment, gantry sensors monitor the temperature and other operating conditions of the x-ray tube 10. Operating the x-ray tube at elevated temperatures above the manufacturers specifications shortens x-ray tube life. Although the scanner will function properly and produce excellent diagnostic images at the elevated x-ray tube temperatures, x-ray tube life may be seriously shortened. Because the x-ray tubes for CT scanners typically cost several tens of thousands of dollars, operating the tubes at temperatures above manufacturers' specifications is a costly reduction in tube life. Another gantry sensor monitors the temperature of the x-ray detectors. Typically, the x-ray detectors include scintillation crystals, photodiodes, and associated amplifiers and circuit components. The photodiodes and other detector components deteriorate more rapidly and fail in a shorter period of time at elevated temperatures. Moreover, thermal noise degradation of the detector signals increases with increased temperature. Thus, operating the scanner with overheated detectors both shortens the life of valuable equipment and causes degradation of the image results. Other gantry operating conditions are also monitored, such as the gantry cooling fans, mechanical rotation and tilt mechanisms, transformer temperatures, and the like. A gantry control 52 and an interface circuit 54 determine which sensed conditions are abnormal and relay the monitored gantry operating conditions to the system monitor via serial condition codes.

Console sensors 50a which monitor central processor operation, temperature, and cooling equipment, and the like are connected directly with system monitor. A comparing means 56 determines whether each sensed console operating condition is abnormal. This determination can be made by sensors which only report abnormal conditions or by comparing a monitored condition level with an acceptable range for that condition in a look-up table 58.

When conditions are unacceptable, the system monitor starts a shut-down timer 60 and enables a message generator 62 or an indicator light 64. The message generator or indicator light advises the operator of the sensed abnormal operating condition. For example, the message generator may print out an appropriate text on the display advising the operator which condition is abnormal, how abnormal the condition is, and how long before the timer 60 will shut down the scanner. Optionally, a display 66 may be provided on the console for counting down the seconds until the system powers down. When the shut-down timer 60 times out, it activates a power down routine 68 which causes a gantry power control 70 to shut down the x-ray tube and other gantry and console components in an orderly manner. Preferably, the power down routine determines whether a scan or scan sequence is in progress and, if so, waits until that scan is completed.

The operator has the option of overriding the timed shut-down. The operator presses an override control 72, such as a touch sensitive area on the screen 24 which resets or overrides the timer 60 and actuates a record routine 74. Preferably, the override command resets the timer or sets it for a longer time period. This provides a repeated reminder to the operator that operation of the scanner should be terminated. Alternately, the timer can be completely overridden or shut-off and operations can continue without further operator intervention. The recording means 74 makes a record of each override in the random access memory 32. The recording means also records an indication of each sensed operating condition which is unacceptable, the level of the condition or parameter, e.g. temperature, a time and date indication, an operating technician identification, and the like.

The system monitor E also blocks the use of unauthorized software and the unauthorized use of authorized software by at least the central processing unit C. Commonly, CT scanners are sold with a variety of standard computer programs and processing techniques. Computer programs for performing additional processing techniques are offered at extra cost. In one embodiment, the central processing unit is preloaded with, or controls processors, firmware, and hardware that are preloaded with the full set of available software, including both purchased and unpurchased software routines The look-up table or memory means 58 is preprogrammed with identifications of the purchased software, i.e. the software routines and associated firmware and hardware to which access is authorized. Each time an operator selects a routine with a routine select region 76 of the touch sensitive screen or other routine selecting means, the comparing means 56 compares the identification of the selected software with the identifications of authorized software in the authorized software table 58. If the software is authorized, the software identification comparing means sends out an enable or authorization signal to the CPU which allows the software to be run.

If the scanner owner desires to purchase additional software routines or lease them for a limited period of time, the authorized software identification table 58 is revised to reflect these changes. More specifically, the manufacturer calls a modem 80 and presents a password to the comparing means 56. If the comparing means finds that the password matches the manufacturers password stored in the look-up table 58, then an authorized software table update means 82 is enabled. The manufacturer can then enter the appropriate additional authorized software identification codes into the authorized software table. Analogously, if the purchaser is returning software or if a lease has expired, the appropriate authorized software identification codes are deleted from the table 58.

In another embodiment, the CPU is not preloaded with all the software. Rather, manufacturers sends a disk with the newly purchased authorized software which is entered in the disk drive 22. The software would include a password which the comparing means 56 compares to the password in the authorized software table 58. If the passwords match, the comparing means enables the central processor unit to load and run the software and enables the update means 86 to enter the software identification into the authorized software table 58. Preferably, the password is unique to each scanner such that the new software disk cannot be used with any other CT scanner.

In either of the preceding embodiments, the operator or a service technician might seek to enter unauthorized third party software or even software of the same manufacturer but intended for a different CT scanner of the same or another model. The comparing means 56 compares identifications of the software which the operator or serviceman is trying to enter with identifications in the authorized software table 58. If the software is unauthorized, the comparing means causes the recording control means 74 to cause identification and other information from the software for which entry is attempted to be recorded into the random access memory 32. Preferably, the identifications include an identification of the original purchaser and the serial number of the scanner for which it was purchased. Sufficient information is recorded to facilitate tracking down the source of any pirate software which an operator or serviceman may try to enter. Optionally, the software comparing means, in response to the attempted entry of unauthorized software, may enable the power down routine 68 to insure that no patients are irradiated under the control of unauthorized software.

The invention has been described with reference to the preferred embodiments. Obviously, modifications and alterations will occur to others upon reading and understanding the preceding detailed description. It is intended that the invention be construed as including all such alterations and modifications insofar as they come within the appended claims or the equivalents thereof.

Having thus described the preferred embodiments, the invention is now claimed to be:

1. A medical diagnostic scanner system comprising:
   a gantry means for receiving a subject, performing a non-invasive examination thereof, and generating electrical examination signals indicative of the non-invasive examination;
   an image reconstruction means for processing the examination signals into operation-readable diagnostic information;
   a central processor unit for controlling the image reconstruction means;
   control panel for selectively controlling the gantry means, the central processor unit and the reconstruction means;
   a system monitor means for selectively interconnecting and enabling the gantry means, the central processor unit, and the control panel;
   a plurality of condition sensors for sensing operating conditions of system components;
   an acceptable operating condition storage means for selectively storing acceptable operating conditions;
   an operating condition comparing means for comparing the sensed operating conditions with the stored acceptable operating conditions;
   a shut-down timing means for cutting off power to the gantry means after a selected duration, the shut-down timing means being operatively connected with the comparing means such that the comparing means causes the timing means to start timing the selected duration;
   an override control means operatively connected with the timing means for enabling an operator to override the timing means during the selected duration and continue operating the gantry means in spite of a sensed unacceptable operating condition;
   a recording means for making a recorded record of each override.

2. The system as set forth in claim 1 wherein the system monitor means further includes a built-in battery back-up for maintaining power in the memory means in which the overrides are recorded.

3. The system as set forth in claim 1 further including an unacceptable operating condition display means for providing the operator with a operator readable display indicative of the sensed unacceptable operating condition.

4. The system as set forth in claim 1 wherein the gantry means includes an x-ray tube for projecting x-rays through the subject, a plurality of detectors for detecting x-rays which have traversed the subject and sensors which monitor at least one of a detector temperature sensing means and an x-ray tube temperature sensing means, and wherein the system monitor means includes a recording means for recording each sensed unacceptable operating temperature.

5. The system as set forth in claim 4 further including a ready control which causes a start up timing means to connect a start control with a gantry power supply means for a preselected duration such that the start control can selectively cause the gantry power supply means to supply power to x-ray tube, whereby supplying power to the gantry means to initiate a diagnostic examination requires actuation of both ready and start switches within the preselected duration.

6. The system as set forth in claim 1 further including:
   a gantry control means for selectively blocking operation of the gantry means;
   a ready control for causing a timer to enable a start control to enable the gantry control means for a selected duration, such that initiation of a diagnostic scan requires depressing both the ready and the start button in order and within the selected duration.

7. The system as set forth in claim 6 further including an indicator means connected with the timer for indicating when the start control is enabled.

8. The system as set forth in claim 1 wherein the plurality of condition sensors include console condition sensors for sensing operating conditions of at least one of the central processor unit, the control panel, the image reconstruction means, and the system monitor means.

9. A medical diagnostic scanner system comprising:
   a gantry means for receiving a subject, performing a non-invasive examination thereof, and generating electrical examination signals indicative of the non-invasive examination;
   an image reconstruction means for processing the examination signals into operation readable diagnostic information;
   a central processing unit for controlling the image reconstruction means;
   a central processor unit for controlling the image reconstruction means, the central processor unit storing a plurality of software routines including authorized and unauthorized routines, each software routine being identified by a software identification;
   a control panel for selectively controlling the gantry means, the central processor unit and the reconstruction means; and,
   a system monitor means for selectively interconnecting and enabling the gantry means, the central processing unit, and the control panel, the system monitor means including:

an authorized software identification memory for storing an updatable list of authorized software identifications;

means for entering an identification of a selected software routine to be performed in the central processing unit;

an authorized software comparing means for comparing the entered software identification with identifications in the authorized software identification memory.

10. The system as set forth in claim 9 further including a modem means operatively connected with the authorized software identification memory for selectively altering the software identifications stored therein.

11. A medical diagnostic scanner system comprising:

a gantry means for receiving a subject, performing a non-invasive examination thereof, and generating electrical examination signals indicative of the non-invasive examination;

an image reconstruction means for processing the examination signals into operation readable diagnostic information;

a central processing unit for controlling the image reconstruction means;

a control panel for selectively controlling the gantry means, the central processing unit and the reconstruction means;

a means for storing software routines, each routine being identified by a unique software identification;

an authorized software identification memory for storing a list of authorized software identifications;

means for entering into the central processing unit an identification of a selected software routine to be performed and an identification of a system in which the selected software routine has been installed;

an embedded authorized software comparing means separate from software in the central processor unit for comparing the entered software identification with identifications in the authorized software identification memory; and, a software loading means for loading software programs from the software storing means into the central processing unit, the comparing means controlling the software loading means for selectively enabling and blocking loading of software into the central processing unit in response to the software identification comparison.

12. The system as set forth in claim 11 further including a recording means for recording software identifications, the recording means being operatively connected with the comparing means to be enabled thereby to record the identifications of software which do not match the authorized software identifications in the authorized software identification memory.

13. The system as set forth in claim 12 further including:

an acceptable operating condition memory means for storing acceptable operating conditions;

a plurality of sensing means for sensing operating conditions;

an operating condition comparing means for comparing the sensed operating conditions with the acceptable operating conditions stored in the acceptable operating parameter memory means; and, the recording means selectively recording the sensing of unacceptable operating conditions.

14. The system as set forth in claim 13 further including a timing means which is enabled by the operating parameter comparing means in response to an unacceptable operating parameter, the timing means being operatively connected with a gantry power control means for terminating the supply of operating power to at least selected gantry means components after a selected duration; and, an override means for overriding the timer and permitting power to be supplied to the selected gantry means components after the selected duration, the recording means recording each override occurrence.

15. A method of controlling a medical diagnostic scanner system, the method comprising:

sensing a plurality of operating conditions of the scanner system;

comparing the sensed operating conditions with acceptable operating conditions;

in response to sensing an unacceptable operating condition, starting to time a shut down time period after which time period an orderly gantry shut down procedure is commenced which shuts down scan subsystems in an orderly manner and terminates operation of the scanner system;

providing a operation readable display indicating the unacceptable operating condition to an operator;

enabling the operator to override the commencement of the orderly shutdown procedure during the time period such that the scanner system continues to operate with the unacceptable condition;

before the completion of the time period, manually overriding the commencement of the orderly shutdown;

during the override, conducting a plurality of scans; and, recording each override.

16. A method of operating a diagnostic scanner system, the method comprising:

storing a plurality of software routines, each routine having a unique identification;

authorizing a selected portion of the routines and changing a list of authorized software routine identifications;

receiving an identification for operator selected software;

comparing the received software identification with the list of authorized software identifications;

in response to the comparison, loading software with an authorized identification into a processor and operating the scanner system with the loaded software; and, blocking the loading of software with an authorized identification into the processor and recording the software identification of unauthorized software.

17. The method as set forth in claim 17 further including:

activating a ready control to start a preselected start time period running;

during the preselected start time period, enabling a start control to initiate a CT scan and after the preselected start time period blocking the start control from initiating the CT scan.

18. The method as set forth in claim 17 wherein activating the ready control includes touching a designated area of a touch sensitive screen.

* * * * *